United States Patent [19]

Gegelys

[11] Patent Number: 4,592,751
[45] Date of Patent: Jun. 3, 1986

[54] INCONTINENCE PAD

[75] Inventor: Anthony A. Gegelys, Somerset, N.J.

[73] Assignee: E. R. Squibb & Sons, Inc., Princeton, N.J.

[21] Appl. No.: 626,264

[22] Filed: Jun. 29, 1984

Related U.S. Application Data

[63] Continuation-in-part of Ser. No. 515,023, Jul. 18, 1983, abandoned.

[51] Int. Cl.⁴ .................. A41B 13/02; A61F 13/16
[52] U.S. Cl. ................... 604/368; 604/375; 604/379; 604/378; 604/380; 604/382
[58] Field of Search ............. 604/375, 366, 379, 382, 604/380, 385, 392, 398, 368, 378

[56] References Cited

U.S. PATENT DOCUMENTS

| | | | |
|---|---|---|---|
| 2,699,170 | 1/1955 | Morin | 128/287 |
| 2,896,627 | 7/1959 | Harwood | 128/290 |
| 3,072,123 | 1/1963 | Davis | 128/284 |
| 3,183,910 | 5/1965 | Patterson | 128/290 |
| 3,211,147 | 10/1965 | Pherson et al. | 128/284 |
| 3,315,676 | 4/1967 | Cooper | 128/287 |
| 3,344,789 | 10/1967 | Arnold et al. | 128/287 |
| 3,431,911 | 3/1969 | Meisel | 128/287 |
| 3,570,492 | 3/1971 | Bettencourt | 128/290 |
| 3,666,611 | 5/1972 | Joa | 161/147 |
| 3,707,430 | 12/1972 | Costanza et al. | 161/123 |
| 3,721,242 | 3/1973 | Krusko | 128/287 |
| 3,769,978 | 11/1973 | DeNight et al. | 128/287 |
| 3,868,287 | 2/1975 | Lewyckyj | 156/201 |
| 3,871,037 | 3/1975 | Willington | 5/91 |
| 3,890,974 | 6/1975 | Kozak | 128/287 |
| 3,897,784 | 8/1975 | Fitzgerald | 128/290 |
| 3,938,522 | 2/1976 | Repke | 128/287 |
| 4,002,171 | 1/1977 | Taft | 128/284 |
| 4,027,672 | 6/1977 | Karami | 128/284 |
| 4,041,949 | 8/1977 | Kozak | 128/287 |
| 4,055,180 | 10/1977 | Karami | 128/287 |
| 4,055,184 | 10/1977 | Karami | 128/287 |
| 4,085,754 | 4/1978 | Ness et al. | 128/287 |
| 4,093,765 | 6/1978 | Schmidt | 428/134 |
| 4,372,309 | 2/1983 | Fowler | 128/284 |

Primary Examiner—George F. Lesmes
Assistant Examiner—Nancy A. B. Swisher
Attorney, Agent, or Firm—Lawrence S. Levinson; Stephen B. Davis

[57] ABSTRACT

The cover sheet includes a moisture permeable top section and moisture impermeable side and bottom sections. The edges of the interior surface of the impermeable section overlap and are joined to the edges of the exterior surface of the permeable section to form an enclosure. A layer of a moisture absorbent core material is situated within the enclosure. A uni-directional barrier layer comprising a laminate of a base or carrier and an absorbent polymer which gels and expands when wetted is interposed between the permeable cover section and the absorbent core. The barrier layer includes a plurality of apertures which decreases in size as the polymer gels and expands.

25 Claims, 5 Drawing Figures

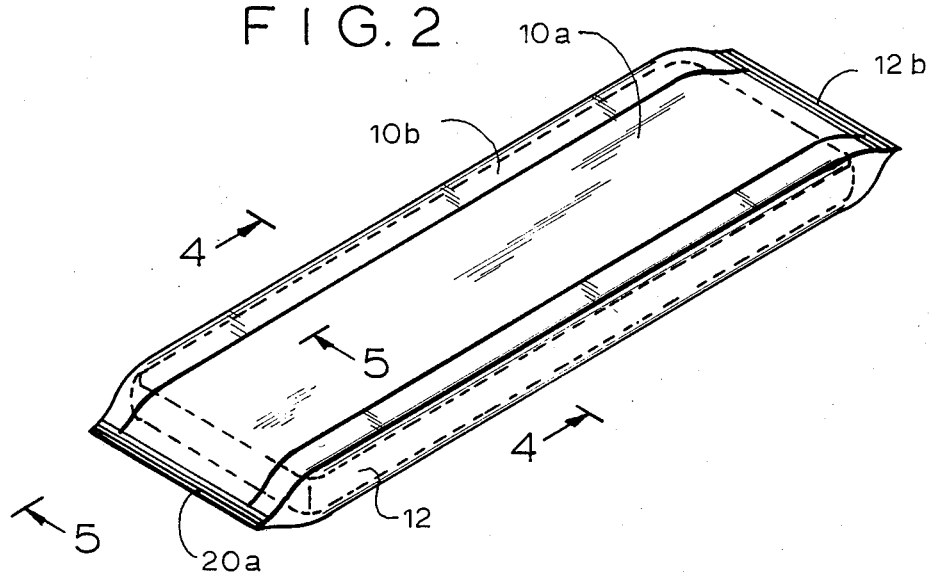
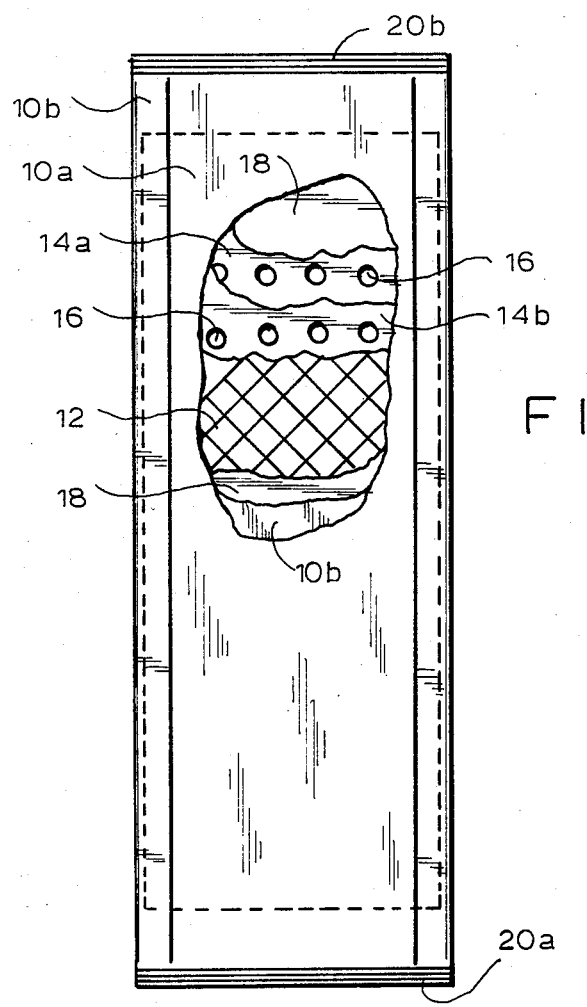

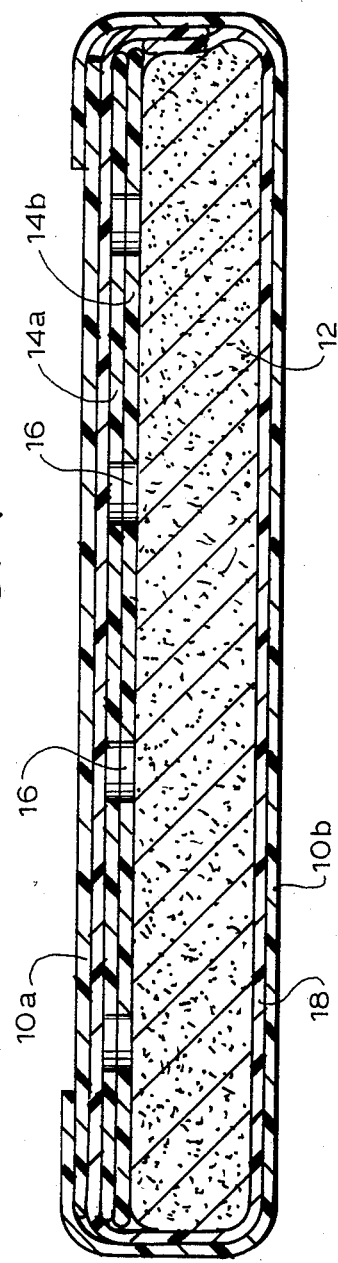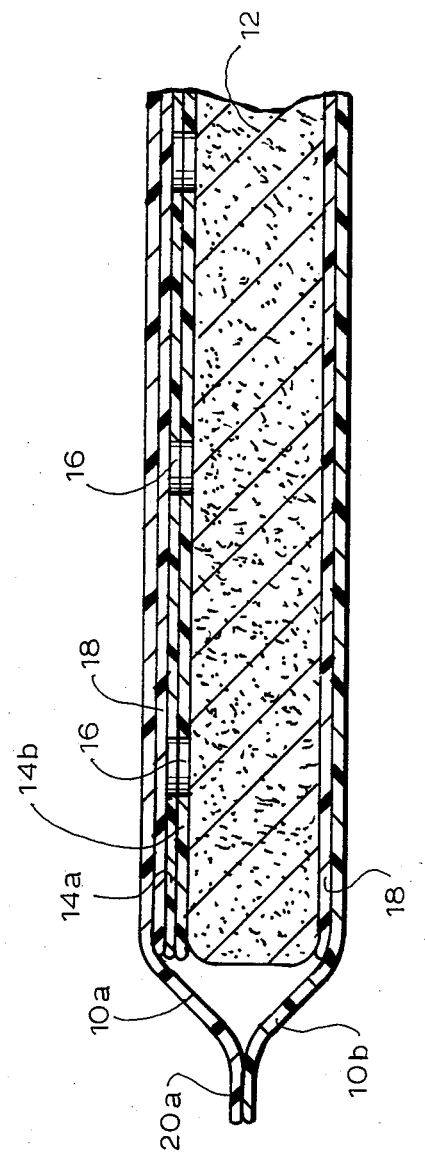

INCONTINENCE PAD

RELATED APPLICATIONS

This application is a continuation-in-part of U.S. Ser. No. 515,023 filed on July 18, 1983 now abandoned.

BACKGROUND OF THE INVENTION

The present invention relates to moisture absorbent pads and, more particularly, to an improved moisture absorbent pad primarily designed for use by incontinence patients.

Incontinence is a malady from which a great many elderly and ill individuals suffer. The inability to restrain or control the discharge of waste material from the body, particularly urine, is a problem which often cannot be remedied and, therefore, it is necessary to provide the incontinent individual with a means for containing the discharge, thereby enabling the individual to lead a relatively normal life.

One successful approach to this problem has been the use of incontinence garments such as briefs or the like, which can be washed and reused. Such garments are provided with a pocket-like structure into which a disposable moisture absorbent incontinence pad can be inserted. The pad, once it becomes moisture laden, is removed from the garment and a new pad is substituted in its place.

Incontinence pads normally include a layer of moisture absorbent core material such as wood pulp, tissue wadding, foams, non-wovens, batting, or the like. The moisture absorbent core material is surrounded by moisture permeable cover sheet which contains the core material and maintains the integrity of the pad. The ends of the cover sheet are usually sealed, by crimping or the like, such that the moisture absorbent core material is completely enclosed by the cover sheet.

In order to increase the absorbency of the core material, the core material may be divided into layers and a moisture diffusable layer interposed therebetween. The moisture diffuser layer may include alternating compressed and stretched zones of tissue or the like and acts to spread the moisture more evenly through the pad to increase its capacity.

Incontinence pads of the type described above suffer from several disadvantages which the improved incontinence pad of the present invention is designed to overcome. One of the problems relates to the tendency of moisture absorbed by the core material to leak from the sides of the pad. This problem becomes particularly acute when the moisture absorbent core material is saturated.

Another problem relates to the tendency of moisture absorbed by the core material to migrate back through the upper surface of the cover sheet towards the wearer, resulting in the pad having a wet, uncomfortable feel.

OBJECTS OF THE INVENTION

It is, therefore, a prime object of the present invention to provide an improved incontinence pad in which the cover sheet is structured to prevent the leakage of moisture from the sides of the pad, even when the absorbent material in the pad is saturated.

It is another object of the present invention to provide an improved incontinence pad which includes a uni-directional moisture barrier which acts to retain moisture in the absorbent material, but permits moisture to pass from the cover sheet to the absorbent core material.

It is another object of the present invention to provide an improved incontinence pad which can be manufactured relatively inexpensively and in which the parts thereof cooperate reliably to provide safe and efficient incontinence control.

SUMMARY OF THE INVENTION

In accordance with the present invention, an incontinence pad is provided comprising a cover sheet having a moisture permeable top section and a moisture impermeable side and bottom section. Means are provided for affixing the edges of the interior surface of the moisture impermeable section to the edges of the exterior surface of the moisture permeable section to form an enclosure. A layer of moisture absorbent core material is situated within the enclosure. A uni-directional moisture barrier layer is interposed between the permeable cover section and the absorbent layer. This uni-directional moisture barrier layer includes a plurality of apertures therethrough.

The barrier layer is a laminate of a "super absorbent" polymer and a base or carrier of paper or the like. Suitable commercially available "super absorbent" polymers include starches, acrylics, modified celluloses, gums and the like. The polymer material may be coated onto a paper base or sandwiched between layers of paper to form the laminate. The "super absorbent" polymer, once it becomes wet, will gel and expand. The apertures in the barrier layer facilitate the movement of moisture from the moisture-permeable section of the cover sheet, through the barrier layer, and into the moisture absorbent core material. As the polymer becomes wet and gels, it expands, thereby reducing the size of the apertures and preventing the moisture from moving back through the barrier layer from the moisture absorbent core material to the cover sheet. Thus, the apertured layer acts to retain moisture in the absorbent core material by functioning as a uni-directional moisture barrier.

The barrier layer of this invention is of a substantially uniform thickness resulting in a pad that absorbs moisture in a predictable manner from one pad to the next unlike prior products where the "super absorbent" is randomly dispersed in the core layer or contained in pockets. Also, the apertures which decrease in size as more moisture contacts the barrier layer provides a way of controlling the amount of moisture reaching the absorbent core and prevents this moisture, when the core becomes saturated, from migrating back through the barrier layer to the liquid permeable cover and the wearer.

The moisture permeable and moisture impermeable sections of the cover sheet form an enclosure. Preferably, at least one end of the enclosure is releasable sealed to permit the material therein, which is bio-degradable, to be removed from the cover sheet and disposed of.

The moisture permeable section of the cover sheet is preferably composed of a non-woven material. The non-woven material is preferably a polyester material. The moisture impermeable section is preferably composed of polyethylene film.

Preferably, a wicking layer is interposed between the cover section and the barrier layer. This wicking layer functions to more uniformally disperse the fluid passing through the permeable cover sheet onto the barrier layer. The wicking layer preferably comprises a layer of moisture permeable tissue material.

BRIEF DESCRIPTION OF THE INVENTION

FIG. 2 is a perspective view of the improved incontinence pad of the present invention;

FIG. 3 is a plan view of the improved incontinence pad of the present invention, showing the layers thereof broken away;

FIG. 4 is a longitudinal sectional view of the improved incontinence pad of the present invention, taken along line 4—4 of FIG. 2; and FIG. 5 is a transverse sectional view of the improved incontinence pad of the present invention, taken along line 5—5 of FIG. 2.

DETAILED DESCRIPTION OF THE INVENTION

Figure 1:
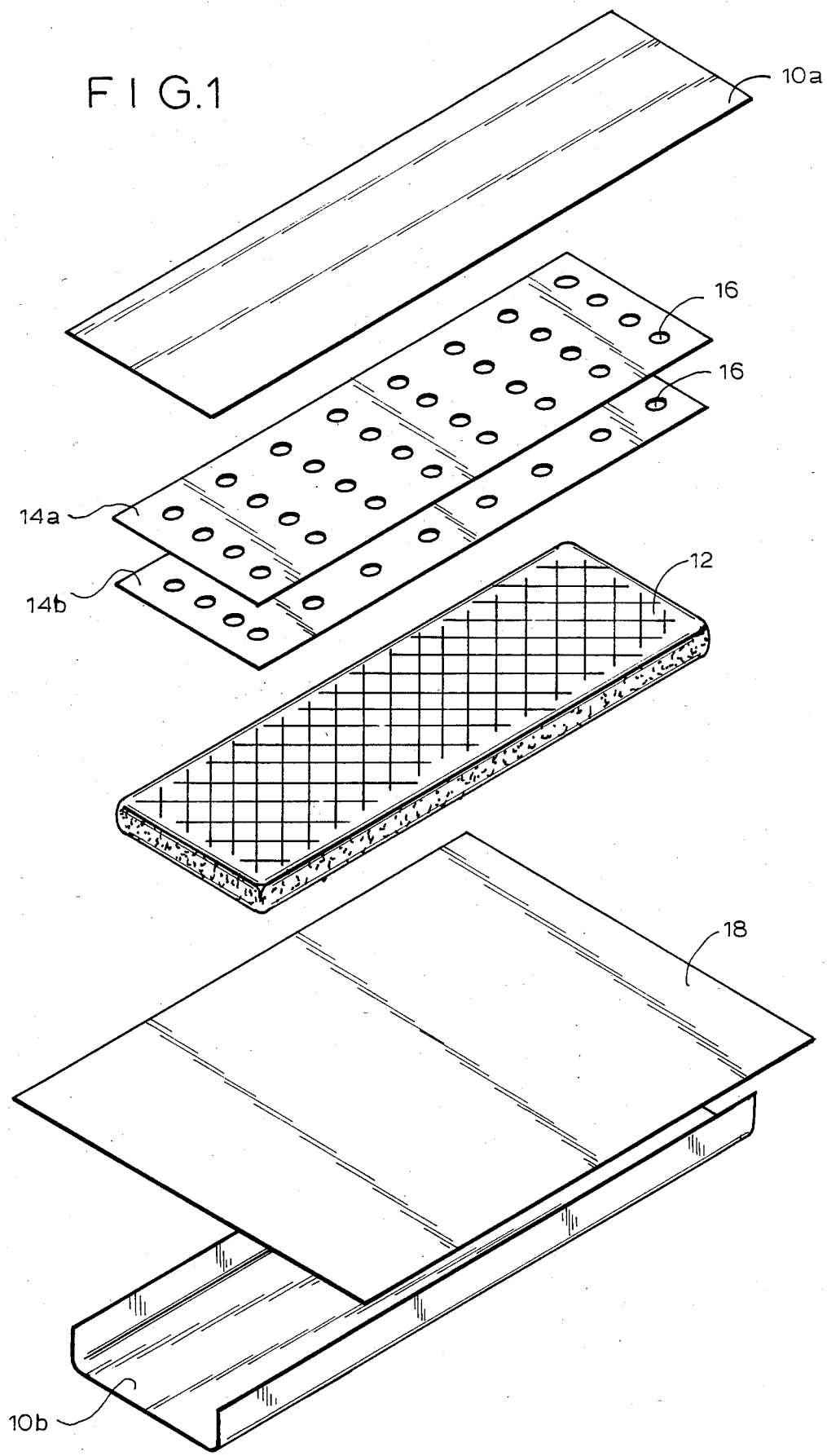
FIG. 1 is an exploded isometric view of the improved incontinence pad of the present invention.

As shown in the figures, the improved incontinence pad of the present invention includes a cover sheet 10 formed of a rectangular liquid permeable top section 10a, and a liquid impermeable side and bottom section 10b. Liquid permeable section 10a is composed of non-woven material made of polyester, polypropylene, or rayon fibers, or the like, which permit the passage of fluid therethrough. The liquid impervious section 10b is preferably formed of polyethylene or polypropylene film or the like.

As illustrated in FIGS. 1 and 4, during manufacture of the pad, the end portions of the moisture impermeable section 10b are folded upwardly, to form the sides of the pad, and then inwardly so as to overlap the edges of the liquid permeable section 10a. The edges of the interior surface of the liquid impermeable section 10b overlap the exterior edges of the liquid permeable section 10a by approximately 0.25 inches to about 0.50 inches. The overlapping surfaces of the liquid impermeable section 10b are then affixed to the exterior edges of liquid permeable section 10a by means of adhesive or the like.

In this manner, the two sections which make up the cover sheet form an enclosure which surrounds the remaining elements of the pad, so as to maintain the integrity thereof. The use of liquid impervious material for the bottom and sides of the pad and in an overlapping relationship with the edges of the liquid permeable top section of the pad, prevents moisture from leaking out the sides or bottom of the pad when the pad is saturated.

In the interior of the enclosure formed by cover sheet 10 is a relatively thick layer of moisture absorbent core material 12, such as fluffed wood pulp, tissue wadding, foams, non-wovens, batting, or the like. Preferably, the exterior of layer 12 is embossed. This embossing enhances the ability of the core material to wick and disperse moisture and also enhances the integrity of the core layer, particularly when wet. As shown in FIGS. 1 and 3, the embossing may be in a diamond-like pattern.

Situated adjacent the top surface of the moisture absorbent layer 12 is a planar, rectangularly shaped uni-directional moisture barrier 14 of uniform thickness. Barrier layer 14 is situated in alignment with the moisture permeable section 10a of cover sheet 10 and functions to retain moisture in the absorbent core layer 12. The "super absorbent" polymer constituent of barrier layer 14 gels and expands when wet. Thus, this layer will act to block the transfer of moisture therethrough. Barrier 14, if formed of an uninterrupted laminate, would gradually restrict the amount of moisture passing therethrough and, finally, after being completely gelled and expanded, would effectively block any moisture from passing into moisture absorbent material 12.

To enhance the amount of fluid, i.e. urine, which can pass through uni-directional barrier layer 14, barrier layer 14 is provided with a large number of apertures 16. The shape, size, and number of apertures can be varied according to the gelling and expansion characteristics of the particular "super absorbent" polymer employed. As layer 14 gradually undergoes the transition which results in gelling and expanding, the swelling of the "super absorbent" polymer substantially decreases the size of the apertures. Thus, the passage of moisture through the barrier layer is gradually reduced, but much more gradually than if no apertures were present.

Accordingly, barrier 14 will act to retain moisture within the absorbent core material by permitting a substantial amount of moisture to pass through it to absorbent core layer 12, but, thereafter, preventing any substantial amount of liquid from passing from absorbent core layer 12 back through barrier 14 to the liquid permeable section 10a of the cover sheet and, thus, back to the wearer. The result is that the top of the pad which is composed of the liquid permeable section 10a, will be more comfortable to the wearer because it will not have a wet feel.

Uni-directional barrier layer 14 may be a single sheet of material, several sheets arranged so that the apertures 16 are aligned as note sheets 14a and 14b in the figures, or a single sheet bent or folded in such a manner that apertures 16 are aligned. Preferred materials for barrier layer 14 are a laminate containing a "super absorbent" starch polymer known as DWAL (trademark of Dow Chemical) and a laminate containing a "super absorbent" modified acrylic polymer known as Gelok 4000 (trademark of Gelok International).

Preferably, moisture absorbent core layer 12 and uni-directional barrier layer 14 are surrounded by a wicking layer 18. This wicking layer, preferably of tissue material, functions to more uniformally disperse the fluid, i.e. urine, passing through permeable cover sheet 10a onto uni-directional barrier layer 14. Thus, wicking layer 18 assures that the "super absorbent" polymer component of barrier layer 14 will gel and expand more uniformly across the entire surface of layer 14.

After barrier 14 is situated on moisture absorbent core layer 12 and wicking layer 18 is wrapped therearound, the interior of the pad is placed on the moisture impermeable section 10b of the cover sheet. The moisture permeable section 10a is then situated on top of layer 18 in alignment with barrier 14 and the edges of the liquid impermeable section 10b are affixed to the exterior surface of the edges of liquid permeable section 10a, by adhesive or the like, as described above.

To finish the pad, the ends 20a, 20b thereof are sealed such as by crimping, heat sealing, ultrasonic welding, gluing, or the like, as illustrated in FIG. 2. Preferably, at least one of ends 20a and/or 20b is sealed in a releasable manner such that the pad interior, which is composed of layers 12, 14, and 18, can be removed from cover sheet 10 for disposal purposes. In this regard, it should be noted that layers 12, 14, and 18 are composed of biodegradable materials which can be flushed down a toilet or the like. However, sections 10a and 10b of the cover sheet are not composed of bio-degradable material and, thus, the interior of the pad must be removed from the cover sheet prior to flushing, if disposal in this manner is desired.

It should now be appreciated that the present invention relates to an improved incontinence pad which eliminates the problems of liquid leakage from the sides of the pad, thereby eliminating the possibility of embarrassing wet spots on the wearer's clothing. Moreover, the uni-directional moisture barrier prevents passage of liquid back to the top of the pad and, thus, the uncomfortable wet feel associated with prior art incontinence pads.

A preferred incontinence pad according to this invention is as follows. Liquid permeable cover sheet 10a is a non-woven polyester material of from about 0.25 to about 2 ounces per square yard, most preferably at about 0.5 ounces per square yard. Liquid impermeable film 10b is a polyethylene film of from about 0.5 mils to about 3 mils, most preferably at about 1 mil thickness. Wicking layer 18, if present, is tissue material at from about 1 to about 3 mils, most preferably about 2 mils thick. Uni-directional barrier layer or layers 14 are preferably of sufficient thickness and include an amount of "super absorbent" polymer so as to absorb from about 30 to about 100 times its weight in urine. Apertures 16 are preferably dimensioned so as to occupy from about 15% to about 35% of the surface area, most preferably about 25% of the surface area, of barrier layer or layers 14 prior to contact with moisture. Moisture absorbent core material 12 is preferably a fluffed wood pulp of about 0.15 inches to about 1.5 inches thick, most preferably about 0.25 to about 0.5 inches.

The exterior surface of liquid impermeable layer 10b may include one or more adhesive strips to aid in securing the pad to a garment.

What is claimed is:

1. An incontinence pad comprising a cover sheet having a moisture permeable section and a moisture impermeable section, a layer of moisture absorbent core material situated within said cover sheet and a uni-directional moisture barrier means interposed between said permeable cover section and said absorbent core layer, said barrier means being of substantially uniform thickness and comprising a laminate containing a super absorbent polymer that expands when wetted, said barrier means having a plurality of apertures extending therethrough, said apertures having a given diameter prior to the expansion of said polymer to facilitate the passage of liquid through said barrier means to said absorbent core layer, the diameter of said apertures decreasing as said polymer expands so as to restrict the passage of liquid back through said barrier layer towards said permeable cover section.

2. The pad of claim 1, further comprising a wicking layer interposed between said cover sheet and said barrier means.

3. The pad of claim 2, wherein said cover sheet has a moisture permeable top section and a moisture impermeable side and bottom section, the edges of the interior surface of said moisture impermeable section are affixed to the edges of the exterior surface of said moisture permeable section to form an enclosure.

4. The pad of claim 3, wherein at least one end of said enclosure is releasably secured.

5. The pad of claim 2, wherein said barrier means is a plurality of apertured sheets, said apertures being substantially aligned, each sheet being of substantially uniform thickness and comprising a laminate of a base or carrier and a polymer that expands when wetted.

6. The pad of claim 5, wherein said polymer is a starch polymer.

7. The pad of claim 5, wherein said polymer is an acrylic polymer.

8. The pad of claim 2, wherein said barrier means is an apertured sheet of substantially uniform thickness folded one or more times such that the apertures are substantially aligned, said sheet comprising a laminate of a base or carrier and a super absorbent polymer that expands when wetted.

9. The pad of claim 8, wherein said polymer is a starch polymer.

10. The pad of claim 8, wherein said polymer is an acrylic polymer.

11. The pad of claim 1, wherein said moisture permeable cover sheet section comprises a non-woven fibrous material.

12. The pad of claim 1, wherein said moisture impermeable cover sheet section is a polyethylene or polypropylene film.

13. The pad of claim 1, wherein said absorbent core material is fluffed wood pulp.

14. The pad of claim 1, wherein the surface of said absorbent core abutting said barrier means is embossed.

15. The pad of claim 2, wherein said wicking layer is tissue and said tissue encompasses said absorbent core material and said barrier means.

16. An incontinence pad comprising a cover sheet having a first section of a non-woven moisture permeable polyester fiber and a second section of moisture impermeable polyethylene film, said sections of said cover sheet being joined to form an enclosure, a core layer of moisture absorbent fluffed wood pulp material, and a uni-directional moisture barrier layer of substantially uniform thickness comprising, a laminate containing a super absorbent polymer that expands when wetted, said barrier layer having a plurality of apertures extending therethrough, said apertures having a given diameter prior to the expansion of said polymer to facilitate the passage of liquid through said barrier layer to said absorbent layer, the diameter of said apertures decreasing as said polymer expands so as to restrict the passage of liquid back through said barrier layer towards said first section.

17. The pad of claim 16, further comprising a wicking layer of tissue material interposed between said cover sheet and said barrier layer.

18. The pad of claim 16, wherein at least one end of said enclosure is releasably secured.

19. The pad of claim 16, wherein said barrier layer is a plurality of apertured sheets, said apertures being substantially aligned, each sheet being of substantially uniform thickness and comprising a laminate of a base or carrier and a super absorbent polymer that expands when wetted.

20. The pad of claim 19, wherein said polymer is a starch polymer.

21. The pad of claim 19, wherein said polymer is an acrylic polymer.

22. The pad of claim 16, wherein said barrier layer is an apertured sheet of substantially uniform thickness folded one or more times such that the apertures are substantially aligned, said sheet comprising a laminate of a base or carrier and a super absorbent polymer that expands when wetted.

23. The pad of claim 22, wherein said polymer is a starch polymer.

24. The pad of claim 22, wherein said polymer is an acrylic polymer.

25. The pad of claim 17, wherein said non-woven moisture permeable polyester fiber is a material of from about 0.25 to about 2 ounces per square yard, said moisture impermeable polyethylene film is from about 0.5 mils to about 3 mils, said tissue wicking layer is from about 1 to about 3 mils, said moisture absorbent fluffed wood pulp core is from about 0.15 inches to about 1.5 inches, and said apertures constitute from about 15% to about 35% of the surface area of said uni-directional barrier layer prior to contact with moisture.

* * * * *